United States Patent [19]

Menke et al.

[11] Patent Number: 5,759,974
[45] Date of Patent: Jun. 2, 1998

[54] BLOCK-FORM CLEANERS FOR FLUSH TOILETS

[75] Inventors: Ronald Menke, Mettmann; Alexander Ditze, Remscheid; Gerd Praus, Krefeld, all of Germany

[73] Assignee: Henkel Kommanditgesellschaft auf Aktien, Duesseldorf, Germany

[21] Appl. No.: 692,806

[22] Filed: Jul. 30, 1996

Related U.S. Application Data

[63] Continuation-in-part of Ser. No. 435,265, May 5, 1995, abandoned.

[30] Foreign Application Priority Data

Nov. 7, 1994 [DE] Germany ............ 44 39 677.5
Oct. 30, 1995 [WO] WIPO ............ PCT/EP95/04245

[51] Int. Cl.$^6$ ............ C11D 17/00; C11D 11/00
[52] U.S. Cl. ............ 510/191; 510/101; 510/192; 510/367; 510/382; 510/392; 510/438; 510/439; 510/440; 510/441; 510/445; 510/446; 510/447; 510/451; 264/148; 264/177.11; 264/241
[58] Field of Search ............ 510/191, 192, 510/101, 382, 392, 367, 438, 439, 440, 441, 445, 446, 447, 451; 264/148, 177.11, 241

[56] References Cited

U.S. PATENT DOCUMENTS

| | | | |
|---|---|---|---|
| 3,856,932 | 12/1974 | May | 424/16 |
| 3,962,107 | 6/1976 | Levin et al. | 510/117 |
| 4,256,599 | 3/1981 | Krisp et al. | 510/117 |
| 4,269,723 | 5/1981 | Barford et al. | 252/106 |
| 4,417,993 | 11/1983 | Gergely | 510/117 |
| 4,522,738 | 6/1985 | Magid et al. | 510/191 |
| 4,578,207 | 3/1986 | Holdt et al. | 252/134 |
| 4,683,072 | 7/1987 | Holdt et al. | 252/102 |
| 4,913,832 | 4/1990 | Kruse et al. | 510/224 |
| 5,571,519 | 11/1996 | Synodis et al. | 424/405 |

FOREIGN PATENT DOCUMENTS

| | | |
|---|---|---|
| 0055100 | 6/1982 | European Pat. Off. . |
| 0101402 | 2/1984 | European Pat. Off. . |
| 0151203 | 8/1985 | European Pat. Off. . |
| 0248936 | 12/1987 | European Pat. Off. . |
| 3225292 | 1/1984 | Germany . |
| 58-168699 | 10/1983 | Japan . |
| 61-291695 | 12/1986 | Japan . |
| 62-036500 | 2/1987 | Japan . |
| 63-182400 | 7/1988 | Japan . |
| 7-109499 | 4/1995 | Japan . |
| 9220774 | 11/1992 | WIPO . |

*Primary Examiner*—Paul Lieberman
*Assistant Examiner*—Lorna M. Douyon
*Attorney, Agent, or Firm*—Ernest G. Szoke; Wayne C. Jaeschke; Henry E. Millson, Jr.

[57] ABSTRACT

Block-form cleaners for flush toilets which consist of at least two masses of different composition, one of the masses being at least partly surrounded by the other mass(es) and the surrounded mass containing an active substance in a concentration at least 1.3 times higher than in the surrounding mass. This distribution ensures that the active substance is more uniformly released over the useful life of the cleaning block.

17 Claims, 3 Drawing Sheets

BLOCK-FORM CLEANERS FOR FLUSH TOILETS

CROSS-REFERENCE TO RELATED APPLICATIONS

This application is a continuation-in-part of U.S. Serial No. 08/435,265 (entitled "Block-Form Cleaners for Flush Toilets", by Menke et al.) filed May 5, 1995, now abandoned, the disclosure of which is incorporated herein by reference.

BACKGROUND OF THE INVENTION

1. Field of the Invention

The present invention relates generally to cleaners in block form and, more particularly, to corresponding cleaners used in the cleaning and disinfection of flush toilets.

2. Statement of Related Art

Cleaners in block form are used to clean toilets above all because it is possible with such cleaners to keep the toilets clean in a substantially automatic manner. The cleaning blocks are either placed in the cistern of flush toilets where they gradually dissolve and release the cleaning agents to the flushing water or, alternatively, are arranged in the toilet bowl in such a way that the flushing water only flows over them every the time the toilet is flushed, the cleaning-active substances being released during this brief period. Cleaning blocks normally also contain perfume. The composition of cleaning blocks has been the subject of numerous proposals of which only those concerned with multicomponent cleaning blocks (EP 55 100, EP 101 402) are to be mentioned here. The multicomponent form was proposed because it enables chemically incompatible active substances or constituents to be accommodated in a single block without any danger of these constituents interacting in storage. One feature common to all known cleaning blocks is that they gradually become smaller in use, their surface steadily diminishing in the process. On the other hand, the amount of perfume and other active substances released to the surrounding environment or to the water flowing past per unit of time is directly dependent upon the available surface of the cleaning block. Accordingly, the quantity of perfume and other active substances released per unit of time also decreases during the use of the cleaning block. Accordingly, to ensure that an adequate quantity of active substance is still released towards the end of the useful life of the cleaning blocks, the composition of the blocks had to be selected in such a way that far more than the necessary quantity of active substance was released per unit of time at the beginning. Although this was generally accepted by the consumer in the case of the cleaning components of the blocks, an overdosage of perfume was often found to be troublesome. However, even the overdosage of cleaning components is questionable on ecological grounds. A technically simple solution to this problem of uniform release of active substances over the useful life of a cleaning block has not yet been proposed.

SUMMARY OF THE INVENTION

Now, the present invention offers a solution to this problem in the form of a cleaning block which consists of at least two masses of different composition, one of the masses being at least partly surrounded by the other mass(es) and the surrounded mass and at least one of the other masses containing at least one identical active substance of which the concentration in the surrounded mass is at least 1.3 times the concentration of the same active substance in the surrounding mass(es). The concentration of this active substance in the surrounded mass is preferably 2 to 10 times as high as in one of the surrounding masses.

Through the particular construction of the new block-form cleaners, only or preponderantly the surface of the mass containing the active substance in the lower concentration is available at the beginning of use for the release of the active substance to the surrounding environment or to the water flowing past. During the use of the cleaning block, this mass is worn away and the surface of the hitherto surrounded mass is exposed so that active substance can also be released from this mass. Since the concentration of active substance in the surrounded mass is distinctly higher than in the surrounding mass, the quantity of active substance released per unit of time again increases so that the reduction in the release of active substance caused by the reduction of the surface is more or less compensated or even overcompensated. In either case, the cleaning blocks according to the invention provide for a considerably more uniform rate of release of the active substance over the useful life of the block than is the case with conventional cleaning blocks. The release characteristic can be finely controlled through the concentration ratios of the active substance in the individual masses and through the geometry and arrangement of the masses relative to one another.

According to the present invention, the mass which contains the active substance in the higher concentration is at least partly surrounded when at least 50% of the surface of the component formed from this mass within the cleaning block as a whole is covered by the other masses so that this part of the surface is not available for the release of active substance at the beginning of use. Preferably at least 70% and, more particularly, at least 80% of the surface should be covered by the other masses. In extreme cases, the mass containing the active substance in the higher concentration may be completely surrounded by the other masses. In a preferred embodiment, the surrounded (inner) mass is only surrounded by one other mass.

Various methods may be used to make the cleaning blocks. Thus, the individual components consisting of the various masses may initially be separately produced and then pressed together, for example under pressure, and optionally shaped at the same time, if desired with addition of binders. In another possible method, however, only one or some of the masses is/are initially molded and the other masses are added in liquid form, the final cleaning block being formed in a casting process with subsequent solidification. A preferred production process for the cleaning blocks according to the invention is the extrusion process in which the individual masses are separately mixed and extruded, the strands issuing from the extruder being shaped and combined in such a way that, after the combined strands have been cut, the required cleaning blocks are directly formed. In a particularly preferred embodiment of the extrusion process, the mass containing the active substance in the higher concentration is extruded in a two-component or multi-component nozzle as a core strand inside a surrounding shell-like strand of the mass containing the active substance in the lower concentration. This process may be controlled in such a way that the strands issue coaxially, although it can also be of advantage for the core strand not to be positioned in the middle of the shell-forming mass. This particular form provides for the production of cleaning blocks in which the surface of the surrounded mass becomes larger gradually rather than suddenly in use.

BRIEF DESCRIPTION OF THE DRAWINGS

Some typical arrangements of the constituent masses in the cleaning blocks are shown in detail in the accompanying drawings. Whereas

DETAILED DESCRIPTION OF THE INVENTION

Figure 1:
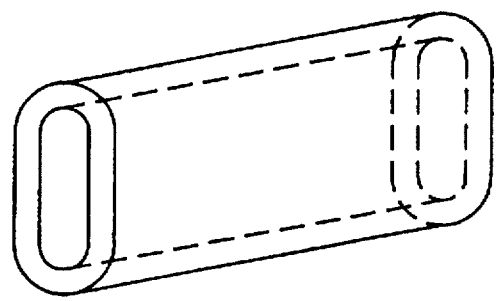
FIGS. 1 to 7 show cleaning blocks consisting of two masses, the cleaning blocks shown in FIGS. 8 and 9 are made up of three masses.

In one preferred embodiment, the ratio by weight of the surrounding mass to the surrounded mass is 1:1 to 2:1.

The composition of the individual masses which together form the cleaning blocks according to the invention may be substantially the same except for the different contents of active substance, although this is by no means essential for the effects achievable in accordance with the invention. These effects can also be achieved when the individual masses differ distinctly from one another in their composition. Accordingly, the composition of the individual masses can also be largely adapted to meet the other requirements arising, for example, in regard to production or storage. Any of the substances hitherto used for the production of cleaning blocks for toilets may be used for the production of the masses. These substances include, in particular, surfactants, disinfectants and bleaches, enzymes, salts, acids, complexing agents, fillers, dyes, perfume, erosion regulators and plasticators. Surfactants, disinfectants, bleaching agents, enzymes, acids, complexing agents, dyes and perfume are regarded as active substances in the context of the present invention whereas such substances as erosion regulators and plasticators, salts and fillers, which for the most part act solely as consistency promoters and moderators for the erosion rate, do not count as active substances in the context of the invention. Preferred active substances in the context of the invention are perfume, complexing agents, acids, disinfectants, bleaches and enzymes, perfume being particularly preferred. Where several substances which count as active substances are present in the cleaning blocks, it is sufficient in accordance with the invention for one of these active substances to satisfy the above-stated requirement that is should be present in the higher concentration in the surrounded mass.

Surfactants from all known classes, namely anionic, nonionic, cationic and amphoteric surfactants, may be selected for use in the cleaning blocks according to the invention, although anionic and/or nonionic surfactants are preferably used. It should be noted that salts of long chain fatty acids (i.e. soaps) are not considered to be surfactants for purposes of the present invention, but are instead classified as erosion regulators, which can be present in one or more of the masses comprising the cleaning blocks of the invention as an optional component in a quantity of from 2 to 25% by weight based on the weight of the mass.

Suitable anionic surfactants are, in particular, those of the sulfate and sulfonate type, although other types, such as salts of fatty acid cyanamides or salts of alkyl ether carboxylic acids obtainable from ethoxylated long-chain alcohols and chloroacetic acid may also be used. The anionic surfactants are mainly used in the form of their sodium salts.

Particularly suitable surfactants of the sulfate type are the sulfuric acid monoesters of primary alcohols of natural and synthetic origin, i.e. the sulfuric acid monoesters of fatty alcohols, for example cocofatty alcohols, tallow fatty alcohols, oleyl alcohol or $C_{10-20}$ oxo alcohols, and those of secondary alcohols with the same chain length. The sulfuric acid monoesters of aliphatic primary alcohols ethoxylated with 1 to 6 moles of ethylene oxide or ethoxylated secondary alcohols or alkylphenols may also be used.

The surfactants of the sulfonate type are, above all, the alkyl benzene sulfonates containing $C_{9-15}$ as alkyl groups and olefin sulfonates, i.e. mixtures of alkene and hydroxyalkane sulfonates and disulfonates of the type obtained, for example, from monoolefins with a terminal or internal double bond by sulfonation with gaseous sulfur trioxide and subsequent alkaline or acidic hydrolysis of the sulfonation products. Other useful surfactants of the sulfonate type are the alkane sulfonates obtainable from $C_{12-18}$ alkanes by sulfochlorination or sulfoxidation and subsequent hydrolysis or neutralization or by addition of bisulfites onto olefins and also the esters of alphasulfofatty acids, for example the alpha-sulfonated methyl or ethyl esters of hydrogenated coconut oil, palm kernel oil or tallow fatty acids.

Suitable nonionic surfactants for the cleaning blocks according to the invention are, in particular, adducts of 1 to 100 and preferably 5 to 60 moles of ethylene oxide (EO) with 1 mole of an aliphatic or alkyl aromatic compound essentially containing 10 to 20 carbon atoms from the group of alcohols, alkylphenols, fatty acids and fatty acid amides, although other types, such as the ethylene oxide adducts with polypropylene oxide and the condensation products of long-chain primary alcohols and reducing sugars, which are also known as alkyl glycosides, may also be used. The adducts of 20 to 50 moles of ethylene oxide with primary alcohols, for example cocofatty alcohols or tallow fatty alcohols, with oleyl alcohol, with oxo alcohols of corresponding chain length or with corresponding secondary alcohol and also with monoalkyl or dialkylphenols containing 6 to 14 carbon atoms in the alkyl radicals are particularly suitable.

Distearyl dimethyl ammonium chloride and alkyl betaine are mentioned as cationic and amphoteric surfactants.

The choice of the surfactants and their percentage content in the individual masses of the cleaning blocks according to the invention is determined by the intended cleaning performance and also by the cooperation of the surfactants with the other constituents not only in the use of the cleaning blocks, but also in their production and storage. Accordingly, of the anionic surfactants mentioned above, alkyl benzene sulfonates, olefin sulfonates and fatty alcohol sulfates are particularly preferred.

Particularly preferred nonionic surfactants are the addition products of ethylene oxide with long-chain aliphatic alcohols containing 12 to 18 carbon atoms and with alkylphenols containing 6 to 12 carbon atoms in the alkyl group, more particularly products in which the average content of ethylene oxide is between 20 and 80 moles per mole of surfactant.

The percentage content of the surfactants in the individual masses of the cleaning blocks according to the invention is preferably between about 7 and about 85% by weight and preferably between about 20 and about 60% by weight. In cases where the cleaning blocks are intended to provide for the uniform release of surfactants to the flushing water over the entire useful life of the blocks, as required in accordance with the invention, the content of surfactants in the surrounding mass is preferably between about 15 and about 35% by weight and preferably between about 20 and about 30% by weight and, in the surrounded mass, is correspondingly higher, surfactant concentrations in the surrounded mass of up to about 85% by weight being entirely possible. It is an advantage of the cleaning blocks according to the invention that even high concentrations of active substance can be tolerated in the surrounded mass even when they provide this mass with a consistency which would be unsuitable for the storage of this mass on its own. By virtue of the surrounding shell of a mass of firmer consistency, these basically unfavorable properties can be compensated to such an extent that the storage of the cleaning blocks is not adversely affected.

Disinfectants are used in the cleaning blocks according to the invention in cases where a germ-inhibiting treatment is required in addition to keeping the toilet clean. To this end, the cleaning blocks according to the invention may preferably contain in one or more of the component masses quantities of up to about 40% by weight and, more particularly, between about 0.5 and about 10% by weight (based on the weight of the component masses) of antimicrobial agents. These antimicrobial agents may emanate from various chemical classes, although compatibility with the other components of the respective masses is an important factor in their choice and also in the choice of other active substances and ingredients. Examples of suitable classes of active substance are phenols, substances which give off active chlorine and substances containing active oxygen. Individual examples from these classes include 1,3-dichloro-5,5-dimethyl hydantoin, bromochloro-5,5-dimethyl hydantoin, 1,3-dichloro-5-ethyl-5methyl hydantoin, sodium dichloroisocyanurate, sodium percarbonate, sodium perborate (monohydrate and tetrahydrate) and magnesium monoperphthalate.

In cases where the cleaning blocks are intended to provide for the uniform release of antimicrobial agents over their entire useful life, as required in accordance with the invention, the concentration of antimicrobial agents in the surrounding mass is preferably between about 0.05 and about 5% by weight, although this quantity is of course largely dependent upon the effectiveness of the particular antimicrobial agent, so that concentrations above or below these limits may be useful in individual cases. In the surrounded mass, the concentration of antimicrobial agents is correspondingly higher. Substances which give off active chlorine and substances containing active oxygen may also be used as bleaching agents in the cleaning blocks according to the invention.

One or more enzymes, such as proteases, lipases and cellulases, may be present in the cleaning blocks according to the invention as an important constituent for supporting the effectiveness of cleaning, particularly against fecal and fat-containing deposits in the toilet and the pipe system. Lipases are particularly effective for eliminating fat-containing deposits. Enzymes which produce active oxygen, such as peroxydases and oxydases, can be of particular advantage by virtue of their bleaching and disinfecting properties. The enzyme content of the cleaning blocks according to the invention in one or more component masses may be up to about 60% by weight and is preferably between about 0.5 and about 30% by weight.

In order to guarantee uniform effectiveness over the useful life of the cleaning blocks, the quantity of enzymes in the surrounding mass is preferably between about 5 and 15% by weight. The surrounded mass contains the enzyme in correspondingly higher concentrations of, preferably, 10 to 30% by weight.

The cleaning blocks according to the invention may contain complexing agents for water hardness and especially for the heavy metal ions often encountered in water, such as those of iron and manganese. Suitable complexing agents are compounds which develop such a strong complexing effect on water hardness and/or on the heavy metal ions mentioned under the in-use conditions of the cleaning blocks that neither water hardness nor heavy metal hydroxides can be precipitated. Examples of suitable classes of complexing agents are aminopolycarboxylic acids, polyphosphonic acids and polymeric polycarboxylic acids and salts thereof and also the salts of hydroxypolycarboxylic acids. The quantities to be used are determined by the complexing capacity of the complexing agents and the intended erosion rate of the cleaning blocks. In general, therefore, the cleaning blocks contain no more than 30% by weight of complexing agent in the individual masses. In most cases, satisfactory results are obtained with quantities of only about 5 to about 25% by weight. If the complexing agent is to be uniformly released over the entire useful life of the cleaning blocks, as required in accordance with the invention, the quantity of complexing agent in the surrounding mass is preferably between about 5 and about 13% by weight. The surrounded mass contains correspondingly higher concentrations.

To prevent limescale deposits and, above all, to remove old coatings from the toilet bowls, acids may also be added as active substances to the cleaning blocks according to the invention providing they are compatible with the other components of the cleaning blocks. Suitable acids are water-soluble, non-volatile acids, more particularly solid acids, which have a $K_S$ value above $10^{-4}$ and preferably above $10^{-2}$ and which do not form poorly soluble calcium salts, for example amidosulfonic acid, phosphoric acid, citric acid, fumaric acid, malic acid, succinic acid and gluconic acid. Their percentage content in the individual masses of the cleaning blocks according to the invention may be up to 30% by weight and is preferably between about 5 and about 25% by weight. Where the cleaning blocks are intended to guarantee the uniform release of these acids over the entire useful life of the blocks, as required in accordance with the invention, the surrounding mass preferably contains between about 7 and about 20% by weight and preferably between about 5 and about 10% by weight of acid. The surrounded mass contains correspondingly higher concentrations.

Dyes may be added to the cleaning blocks according to the invention as a visual demonstration of their effectiveness. The dyes used are preferably water-soluble dyes generally blue and green in color. An important factor in the choice of the dyes is that they should be compatible with the other constituents of the cleaning blocks and that they should not have a substantive effect on the ceramic surfaces of the toilet bowls. Examples of suitable dyes are triaryl methane dyes, such as the triphenyl methane dye with the Color Index No. 42090.

The quantity of dye in the cleaning blocks according to the invention is determined by the required effect and is preferably not more than 25% by weight and, more particularly, is between about 3 and about 20% by weight, based on the overall composition of the dye-containing component mass of the cleaning block. Where the cleaning blocks are intended to guarantee the uniform release of dyes over their entire useful life, the surrounding mass preferably contains between about 3 and about 15% by weight and more preferably between about 3 and about 10% by weight of dye while the surrounded mass contains correspondingly higher concentrations of the dye. If the dyes are mainly intended to color the mass, other dyes, such as pigment dyes or oil-soluble dyes, may also be used, but in far smaller quantities; e.g. in most cases, less than 0.1% by weight generally being sufficient.

A particularly preferred active substance in the cleaning blocks according to the invention is perfume. The gradual disappearance of fragrance in addition to the reduction in the intensity of color of the flushing water in conventional cleaning blocks is regarded as a particular disadvantage by the consumer. Accordingly, the uniform release of fragrances from the cleaning blocks according to the invention is a particularly noticeable advantage. The choice of suitable fragrances is limited solely by possible interactions with other constituents of the individual masses of the cleaning blocks. The total fragrance content of the individual masses of the cleaning blocks according to the invention is preferably no more than 20% by weight and, more particularly, is between about 4 and about 15% by weight. If importance is attached to the uniform release of fragrances throughout the useful life of the cleaning blocks, as required in accordance with the invention, the surrounding mass preferably contains between about 3 and about 8% by weight and, more particularly, between about 4 and about 6% by weight of perfume while the surrounded mass contains correspondingly larger quantities. In this case, too, the composition of the cleaning blocks according to the invention has an advantageous effect in the respect that the surrounded mass can contain very high concentrations of perfume oil because its consistency is not crucial to the stability of the blocks in storage which is largely determined by the consistency of the surrounding masses.

The substances referred to as erosion regulators are mainly intended to control the consumption of the cleaning blocks in use in such a way that they remain effective to the end of their intended useful life. Preferred regulators are solid long-chain fatty acids, such as stearic acid, and also salts of such fatty acids, fatty acid ethanolamides, such as cocofatty acid monoethanolamide, fatty alcohols preferably containing 12 to 18 carbon atoms or solid polyethylene glycols, such as those with molecular weights of 1,500 to 50,000. In general, no more than 25% by weight of erosion regulators are needed in the individual masses. Preferred contents are about 2% by weight to about 15% by weight. The type and quantity of erosion regulators may vary in the individual component masses of the cleaning blocks according to the invention.

Plasticators are mainly intended to provide the cleaning masses with a plasticity suitable for the molding of the blocks. Plasticators are high-boiling organic substances which are liquid at the processing temperature. Suitable plasticators are, for example, paraffin oils, 1,2-propylene glycol, silicone oils, phthalic acid esters, terpenes and dihydroabietic acid esters. Dihydroabietic acid methyl ester, diethyl phthalate and dibutyl phthalate are preferably used. Since the function of the plasticators can often be performed by other constituents of the cleaning blocks, above all by the perfume oils, but also by nonionic surfactants or liquid acids, their presence is only necessary in a few cases. In such cases, they are used in quantities of up to 15% by weight.

The consistency and erosion behavior of the cleaning blocks can also be influenced by the addition of inorganic salts, although this component also improves the homogeneity of the blocks in critical cases. In addition, the salts can enhance the cleaning effect of the surfactants by electrolyte effects and as buffers. They can act as hardness-binding agents, as for example in the case of polyphosphates, and as consistency promoters, as in the case of alkali metal silicates. The alkali metal or ammonium salts of mineral acids, optionally in hydrated form, are generally used as the salts. The sodium salts of sulfuric acid, phosphorus acids, carbonic acid and hydrochloric acid are preferred. They are used in quantities of up to about 60% by weight and preferably in quantities of from about 10 to about 40% by weight in the individual masses, the type and quantity again being variable within the individual component masses.

In addition to the ingredients already mentioned, the cleaning blocks according to the invention may contain additives typically encountered in block-form toilet cleaners to round off the property spectrum of the cleaning blocks. Examples of such additives include fillers and preservatives. Fillers, which may even be insoluble in water, such as cellulose powder for example, act inter alia as bulk promoters or as consistency regulators and can eliminate any tackiness present in the masses. The function of preservatives is to keep the cleaning blocks free from microbial contamination in storage and in use.

The use of the cleaning blocks according to the invention is no different from the use of the block-form cleaners hitherto used for this purpose. Blocks which are intended to be used in the cistern of the toilet are either placed therein as such or are arranged therein in cage-like containers in such a position that they can be reached by the inflowing water or by the stored water. Cleaning blocks intended for use in the toilet bowl are arranged in suitable holders or in basket- or cage-like containers in the toilet bowl at a place where the incoming flushing water flows past whenever the toilet is flushed. They are normally suspended from the inner rim of the toilet bowl.

EXAMPLES

In the following Examples, the composition of the individual masses of which the cleaning blocks consist is shown first of all. Unless otherwise indicated, the figures represent percentages by weight; pbw stands for parts by weight. The weights of the cleaning blocks and the weights of the component masses of which they consist are then shown. Particulars of the production and property testing of the cleaning blocks follow thereafter.

EXAMPLE 1:

| WC stick containing liquid disinfectant | | |
|---|---|---|
| Raw material | Shell | Core |
| Sodium lauryl sulfate | 12.0% | 12.0% |
| Tallow alcohol + 25 EO | 28.0% | 28.0% |
| Cocofatty acid monoethanolamide | 5.0% | 5.0% |
| Cellulose powder | 6.0% | 6.0% |
| Na citrate (dihydrate) | 5.0% | 5.0% |
| $Na_2SO_4$ | 34.0% | 32.0% |
| $Na_2CO_3$ | 2.0% | 2.0% |
| Perfume oil | 4.0% | 4.0% |
| Palmitic/stearic acid mixture (1:1) | 2.0% | 2.0% |
| Liquid disinfectant Bodoxin ™ (Bode-Chemie) | 2.0% | 4.0% |
| Total weight 50 g: | Shell 25 g | Core 25 g |

Production Process:

The powder-form raw materials of the shell and core were premixed in two separate mixers and stored in two silos. The two mixtures were introduced into extruders 1 (shell) and 2 (core) via two weighing belts. The various disinfectant components were introduced into extruders 1 and 2 in the form of a mixture with perfume oil through metering pumps. The strands were combined in a ratio by weight of 1:1 in a multi-component nozzle and were cut to the required length by an automatic cutting unit. The stick had the shape shown in FIG. 1 with external dimensions of approximately 15×27× 86 mm.

EXAMPLE 2:

WC stick containing powder-form disinfectant

| Raw material | Shell | Core |
| --- | --- | --- |
| Sodium lauryl sulfate | 9.0% | 9.0% |
| Tallow alcohol + 25 EO | 28.0% | 28.0% |
| Cocofatty acid monoethanolamide | 9.0% | 9.0% |
| Cellulose powder | 6.0% | 6.0% |
| Na citrate (dihydrate) | 5.0% | 5.0% |
| $Na_2SO_4$ | 35.0% | 33.5% |
| $Na_2CO_3$ | 1.5% | 1.5% |
| Perfume oil | 5.0% | 5.0% |
| Diazolindinyl urea (Germall ™ II) | 1.5% | 3.0% |
| Total weight 50 g: | Shell 25 g | Core 25 g |

Figure 2:
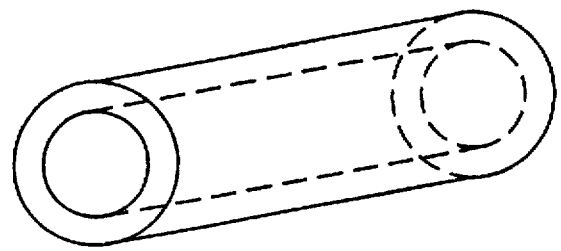

Production Process:

Production was carried out as described in Example 1, except that the powder-form disinfectant was introduced into the separate mixers in the corresponding concentrations and homogeneously mixed with the other powder raw materials. Round sticks approximately 24 mm in diameter and approximately 80 mm in length (FIG. 2) with a total weight of 50 g (shell 25 g, core 25) were cut and packed in water-soluble film.

EXAMPLE 3:

Cistern cubes with a disinfecting effect

| Raw material | Shell | Core |
| --- | --- | --- |
| Sodium dodecyl benzene sulfonate (Ufaryl ™ DL 80 CW; 80% DBS, 13% $Na_2SO_4$, 5% Na citrate 2% free oil) | 47.5% | 44.0% |
| $Na_2SO_4$ | 15.0% | —% |
| Xanthan (Rhodopol ™ 50 MD) | 2.0% | 4.0% |
| Dihydroabietic acid methyl ester (Hercolyn ™ D) | 12.0% | 12.0% |
| Na dichloroisocyanate dihydrate | 23.5% | 40.0% |
| Total weight 50 g: | Shell 25 g | Core 25 g |

Figure 7:
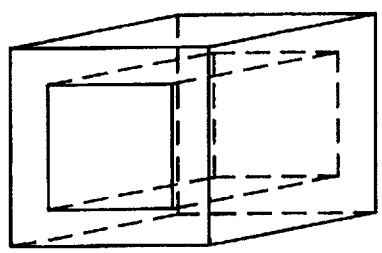

The raw material components were mixed in a separate Z-kneader with addition of the plasticator (Hercolyn™ D) in a batch size of 150 kg and plasticated. The two components were introduced into the corresponding mold via discharge screws and were combined in a twin die ring to form a cube with an edge length of around 34 mm (FIG. 7).

For an erosion rate of 21 flushings/day, the 50 g cubes had a life of around 400 flushings. With hourly flushing, an active chlorine content sufficient for disinfection of 0.3 to 1.0 ppm could be detected in the flushing water.

EXAMPLE 4:

WC stick with a relatively high fragrance content in the cast core

| Raw material | Shell | Core |
| --- | --- | --- |
| Sodium lauryl sulfate | 14.0% | —% |
| Cocofatty acid monoethanolamide | 3.0% | —% |
| Tallow alcohol + 25 EO | 21.0% | 65.0% |
| Cellulose powder | 8.0% | —% |
| Na citrate (dihydrate) | 7.5% | —% |
| $Na_2SO_4$ | 36.0% | —% |
| $Na_2CO_3$ | 2.5% | —% |
| Perfume oil | 5.0% | 15.0% |
| Palmitic/stearic acid mixture (1:1) | 3.0% | 5.0% |
| Polyethylene glycol 1500 | —% | 15.0% |
| Total weight 50 g: | Shell 35 g | Core 15 g |

Figure 4:
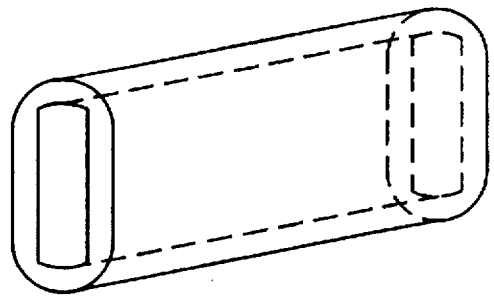

Production Process:

After the raw materials had been premixed and the hollow shell extruded, the shell was cut to its final length and placed on a support in such a way that the molding was closed underneath. The raw material components of the core were melted in a heatable vessel and mixed while stirring with perfume oil. The hollow shells were filled by means of a casting trolley and passed through a cooling duct. The cooled samples were packed in a corresponding container and hermetically sealed with cellophane. The stick shown in FIG. 4 had external dimensions of 15×27×88 mm.

Under standard flushing conditions, the stick had a life of approximately 280 flushings.

The advantage of this embodiment is the possibility of incorporating very large quantities of perfume in the core. A particularly uniform fragrance impression was achieved over the useful life of the stick.

EXAMPLE 5:

Extruded two-phase stick with a fragrance intensive core

| Raw material | Shell | Core |
| --- | --- | --- |
| Sodium lauryl sulfate | 12.0 pbw | Same |
| Tallow alcohol + 25 EO | 28.0 pbw | basic |
| Cocofatty acid monoethanolamide | 3.0 pbw | mixture |
| Cellulose powder | 6.0 pbw | |
| Na citrate (dihydrate) | 5.0 pbw | |
| $Na_2SO_4$ | 36.0 pbw | |
| $Na_2CO_3$ | 2.0 pbw | |
| Palmitic/stearic acid mixture (1:1) | 3.0 pbw | |
| Perfume oil citrus note | 5.0 pbw | 9.0 pbw |
| Total weight 50 g: | Shell 25 g | Core 25 g |

Production Process:

The shell and core were prepared from the same basic mixture. To this end, the powder-form raw materials were combined in a mixer and transferred to a storage silo. They were then introduced into two separate extruders via a weighing belt with a quantity divider. The different perfume components were sprayed into each extruder via metering pumps. The two-phase strands were discharged via a special double head by means of a Bepex molding press and cut to the required length by a pneumatic cutter. The sticks shown in FIG. 2 had an external diameter of around 24 mm for a length of about 80 mm.

This process is particularly advantageous because there is no need for a second mixing unit with a storage container and weighing belt. In the standard test, this stick had a useful life of 250 flushings.

EXAMPLE 6:

Extruded two-phase stick with a fragrance intensive core

| Raw material | Shell | Core |
|---|---|---|
| Sodium lauryl sulfate | 14.0 pbw | Same |
| Tallow alcohol + 25 EO | 19.0 pbw | basic |
| Cocofatty acid monoethanolamide | 6.0 pbw | mixture |
| Cellulose powder | 8.0 pbw | |
| Na citrate (dihydrate) | 7.5 pbw | |
| Na$_2$SO$_4$ | 34.55 pbw | |
| Na$_2$CO$_3$ | 0.95 pbw | |
| Myristyl alcohol (Lorol ™ C$_{14}$) | 5.0 pbw | |
| Perfume oil flowery note | 5.0 pbw | 11.0 pbw |
| Total weight 50 g: | Shell 32 g | Core 18 g |

Figure 5:
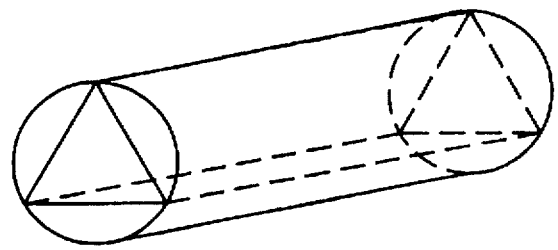

The production process corresponded to Example 5 except that a mold of the type shown in FIG. 5 (approx. 24×80 mm) was used. This embodiment is particularly advantageous because, with increasing consumption, the more highly perfumed intensive core was continuously exposed by flushing. The sticks had a useful life of 320 flushings under standard conditions.

EXAMPLE 7:

Extruded two-phase stick with a fragrance intensive core

| Raw material | Shell | Core |
|---|---|---|
| Sodium lauryl sulfate | 15.0 pbw | Same |
| Tallow alcohol + 25 EO | 15.0 pbw | basic |
| Cocofatty acid monoethanolamide | 6.0 pbw | mixture |
| Cellulose powder | 3.0 pbw | |
| Na citrate (dihydrate) | 3.5 pbw | |
| Na$_2$SO$_4$ | 36.5 pbw | |
| Na$_2$CO$_3$ | 2.0 pbw | |
| Sodium dodecyl benzene sulfonate | 15.0 pbw | |
| Perfume oil apple note | 4.0 pbw | 6.0 pbw |
| Total weight 50 g: | Shell 25 g | Core 25 g |

The production process corresponded to Example 5 except that a mold of the type shown in FIG. 1 (measuring approximately 15×27 ×84 mm) was used.

The sticks had a useful life of 300 flushings in the standard test.

EXAMPLE 8:

Cistern blocks

| Raw material | Shell | Core |
|---|---|---|
| Sodium lauryl sulfate | 19.0% | 19.0% |
| Cocofatty acid monoethanolamide | 33.0% | 33.0% |
| Na citrate (dihydrate) | 5.0% | 5.0% |
| Na$_2$SO$_4$ | 18.0% | 14.0% |
| Na$_2$CO$_3$ | 2.0% | 2.0% |
| Acid Blue 9 | 15.0% | 15.0% |
| Perfume oil flowery note | 8.0% | 12.0% |
| Total weight 100 g: | Shell 50 g | Core 50 g |

Figure 3:
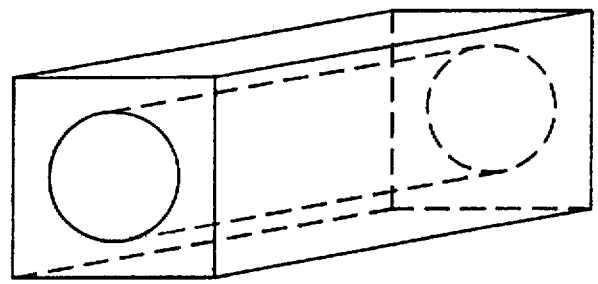

The production process correspond to Example 3. Blocks corresponding to FIG. 3 and to FIG. 6, each with external dimensions of 34×34×68 mm, were produced. In both cases, the blocks had a useful life in the standard test of around 1,400 flushings. The fragrance was given off very uniformly from both types of block.

EXAMPLE 9:

Cistern blocks

| Raw material | Shell | Core |
|---|---|---|
| Sodium lauryl sulfate | 11.4% | 11.4% |
| Cocofatty acid monoethanolamide | 8.5% | 8.5% |
| Na citrate (dihydrate) | 9.0% | 18.5% |
| Na$_2$SO$_4$ | 58.3% | 47.8% |
| Na$_2$CO$_3$ | 0.8% | 0.8% |
| Acid Blue 9 | 4.0% | 4.0% |
| Sodium stearate | 2.0% | 2.0% |
| Perfume oil spruce note | 6.0% | 6.0% |
| Total weight 100 g: | Shell 60 g | Core 40 g |

The production process corresponded to Example 3. Blocks corresponding to FIG. 3 and to FIG. 6 each with external dimensions of approximately 32×32×66 mm were produced. In both cases, the blocks had a useful life in the standard test of around 1,100 flushings. The inhibiting effect against lime deposits remained substantially constant throughout the period of use.

EXAMPLE 10:

Cistern blocks

| Raw material | Shell | Core |
|---|---|---|
| Sodium lauryl sulfate | 19.0% | 19.0% |
| Cocofatty acid monoethanolamide | 35.0% | 35.0% |
| Na$_2$SO$_4$ | 10.0% | —% |
| Na$_2$CO$_3$ | 2.5% | 2.5% |
| Acid Blue 9 | 15.0% | 15.0% |
| Acrylic acid/maleic acid copolymer (Sokalan ™ CP 5) | 12.5% | 22.5% |
| Perfume oil spruce note | 6.0% | 6.0% |
| Total weight 100 g: | Shell 50 g | Core 50 g |

The production process corresponded to Example 3. Blocks corresponding to FIG. 3 and to FIG. 6 each with external dimensions of approximately 34×34×68 mm were produced. In both cases, the blocks had a useful life in the standard test of approximately 550 flushings. The inhibiting effect against lime deposits remained substantially constant through the period of use.

EXAMPLE 11:

Cistern blocks

| Raw material | Shell | Core |
|---|---|---|
| Sodium lauryl sulfate | 15.0% | 15.0% |
| Cocofatty acid monoethanolamide | 35.0% | 35.0% |
| Na$_2$SO$_4$ | 13.5% | —% |
| Sodium stearate | 8.0% | 7.0% |
| Acid Blue 9 | 7.5% | 15.0% |
| Citric acid | 15.0% | 25.0% |
| Perfume oil wintergreen | 6.0% | 3.0% |
| Total weight 100 g: | Shell 50 g | Core 50 g |

The production process corresponded to Example 3. Blocks corresponding to FIG. 3 and to FIG. 6 each with external dimensions of approximately 34×34×68 mm were produced. In both cases, the blocks had a useful life in the standard test of approximately 1,600 flushings. The inhibiting effect against lime deposits remained substantially constant throughout the period of use.

EXAMPLE 12:

| Raw material | Shell | Core |
| --- | --- | --- |
| Sodium lauryl sulfate | 11.2% | 11.2% |
| Cocofatty acid monoethanolamide | 8.5% | 8.5% |
| Na$_2$SO$_4$ | 57.5% | 54.5% |
| Sodium stearate | 3.0% | 3.0% |
| Na$_2$CO$_3$ | 0.8% | 0.8% |
| Acid Blue 9 | 4.0% | 7.0% |
| Na citrate (dihydrate) | 9.0% | 9.0% |
| Perfume oil citrus | 6.0% | 6.0% |
| Total weight 100 g: | Shell 50 g | Core 50 g |

The production process corresponded to Example 3. Blocks corresponding to FIG. 3 and to FIG. 6 each with external dimensions of approximately 32×32×66 mm were produced. In both cases, the blocks had a useful life in the standard test of approximately 1.000 flushings. The coloring of the toilet flushing water remained substantially constant throughout the period of use.

EXAMPE 13:

Extruded two-phase stick with lime inhibiting intensive core

| Raw material | Shell | Core |
| --- | --- | --- |
| Sodium lauryl sulfate | 14.0% | 14.0% |
| Tallow alcohol + 25 EO | 21.5% | 16.5% |
| Cocofatty acid monoethanolamide | 3.0% | 3.0% |
| Cellulose powder | 8.0% | 8.0% |
| Na citrate (dihydrate) | 5.0% | 10.0% |
| Na$_2$SO$_4$ | 37.0% | 37.0% |
| Na$_2$CO$_3$ | 2.5% | 2.5% |
| Palmitic/stearic acid mixture (1:1) | 3.0% | 3.0% |
| Perfume oil | 6.0% | 6.0% |
| Total weight 50 g: | Shell 30 g | Core 20 g |

The production process corresponded to Example 1. The shape shown in FIG. 4 was selected with external dimensions of approximately 15×27×86 mm. The stick had a useful life in the standard test of 300 flushings and a very uniform inhibiting effect.

EXAMPLE 14:

Extruded two-phase stick with lime inhibiting intensive core

| Raw material | Shell | Core |
| --- | --- | --- |
| Sodium lauryl sulfate | 14.0% | 14.0% |
| Tallow alcohol + 25 EO | 19.0% | 17.0% |
| Cocofatty acid monoethanolamide | 3.0% | 3.0% |
| Cellulose powder | 8.0% | 8.0% |
| Na$_2$SO$_4$ | 36.5% | 34.0% |
| Na$_2$CO$_3$ | 2.0% | 2.0% |
| Myristyl alcohol | 4.0% | 4.0% |
| Sodium gluconate | 7.5% | 12.0% |
| Perfume oil | 6.0% | 6.0% |
| Total weight 50 g: | Shell 30 g | Core 20 g |

The production process corresponded to Example 1. The shape shown in FIG. 5 (approx. 24×80 mm) was selected. The stick had a useful life in the standard test of 260 flushings and a very uniform inhibiting effect.

EXAMPLE 15:

Extruded two-phase stick with lime inhibiting intensive core

| Raw material | Shell | Core |
| --- | --- | --- |
| Sodium lauryl sulfate | 14.0% | 14.0% |
| Tallow alcohol + 25 EO | 19.0% | 19.0% |
| Cocofatty acid monoethanolamide | 3.0% | 3.0% |
| Cellulose powder | 8.0% | 8.0% |
| Na$_2$SO$_4$ | 37.5% | 33.0% |
| Myristyl alcohol | 5.0% | 5.0% |
| Fumaric acid | 7.5% | 12.0% |
| Perfume oil | 6.0% | 6.0% |
| Total weight 50 g: | Shell 25 g | Core 25 g |

The production process corresponded to Example 1. The shape shown in FIG. 1 with external dimensions of 15×27×86 mm was selected. The stick had a useful life in the standard test of 250 flushings and a very uniform inhibiting effect.

EXAMPLE 16:

Extruded two-phase stick with lime inhibiting intensive core

| Raw material | Shell | Core |
| --- | --- | --- |
| Sodium lauryl sulfate | 18.0% | 18.0% |
| Tallow alcohol + 25 EO | 20.0% | 20.0% |
| Cocofatty acid monoethanolamide | 3.0% | 3.0% |
| Cellulose powder | 20.0% | 15.0% |
| Na$_2$SO$_4$ | 23.0% | 23.0% |
| Palmitic/stearic acid mixture (1:1) | 2.0% | 2.0% |
| Citric acid | 10.0% | 15.0% |
| Perfume oil | 4.0% | 4.0% |
| Total weight 50 g: | Shell 25 g | Core 25 g |

The production process corresponded to Example 1. The shape shown in FIG. 2 (approximately 24 x 86 mm) was selected. The stick had a useful life in the standard test of 300 flushings and a very uniform inhibiting effect.

EXAMPLE 17:

WC stick with two phases and a barrier layer

| Raw material | Shell | Core 1 | Core 2 |
| --- | --- | --- | --- |
| Sodium lauryl sulfate | 12.0 pbw | | |
| Tallow alcohol + 25 EO | 28.0 pbw | 60.0 pbw | |
| Cocofatty acid monoethanolamide | 3.0 pbw | | |
| Cellulose powder | 6.0 pbw | | Same |
| Na citrate (dihydrate) | 5.0 pbw | | basic |
| Na$_2$SO$_4$ | 35.0 pbw | | mixture |
| Na$_2$CO$_3$ | 2.0 pbw | | as shell |
| Palmitic/stearic acid mixture (1:1) | 4.0 pbw | | |
| Polyethylene glycol 1500 | | 40.0 pbw | |
| Perfume oil citrus note | 5.0 pbw | | 9.0 pbw |
| Total weight 50 g: | 25.0 g | 5.0 g | 20.0 g |

Figure 8:
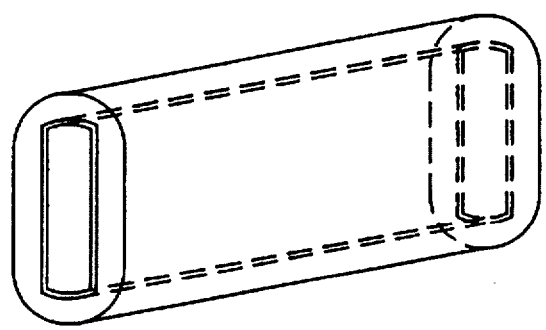

Production process:

The shell and core 2 were prepared from the same basic mixture. The powder-form raw materials were combined in a mixture and transferred to a storage silo. The raw materials of core 1 were melted in a heated vessel. Extrusion was carried out in a triple Bepex molding press by introduction of the melt as a barrier layer in a thickness of 1 mm between the shell and core 2. The stick shown in FIG. 8 had external dimensions of approximately 15×27×86 mm.

The barrier layer prevented the perfume from migrating from core 2 into the shell. The stick had a useful life in the standard test of 280 flushings.

EXAMPLE 18:

Extruded three-phase stick with fragrance intensive core

| Raw material | Shell | Core 1 | Core 2 |
|---|---|---|---|
| Sodium lauryl sulfate | 12.0 pbw | | |
| Tallow alcohol + 25 EO | 28.0 pbw | | |
| Cocofatty acid monoethanolamide | 3.0 pbw | | |
| Cellulose powder | 6.0 pbw | Same | |
| Na citrate (dihydrate) | 5.0 pbw | basic | |
| $Na_2SO_4$ | 36.0 pbw | mixture | |
| $Na_2CO_3$ | 2.0 pbw | as shell | |
| Palmitic/stearic acid mixture (1:1) | 4.0 pbw | | |
| Perfume oil citrus note | 4.0 pbw | 8.0 pbw | 10.0 pbw |
| Total weight 50 g: | 25.0 g | 20.0 g | 10.0 g |

Figure 9:
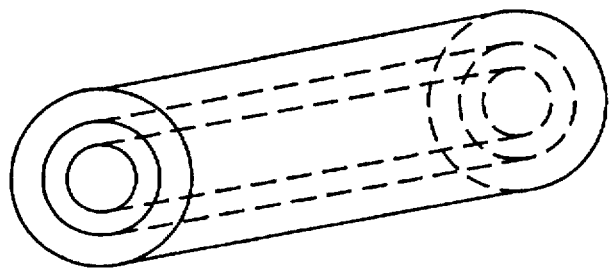

Production Process:

A basic mixture was used. The individual phases were introduced into three separate extruders via weighing belts. The perfume was sprayed into each extruder via metering pumps. In a Bepex molding press with a triple head, the strands were discharged and subsequently cut to size. The shape corresponded to FIG. 9 with external dimensions of approximately 24×80 mm.

The sticks had a useful life in the standard test of 300 flushings and a particularly uniform release of fragrance.

EXAMPLE 19:

WC stick containing lipase

| Raw material | Shell | Core |
|---|---|---|
| Sodium lauryl sulfate | 12.6% | 12.6% |
| Tallow alcohol + 25 EO | 16.0% | 16.0% |
| Cocofatty acid monoethanolamide | 6.0% | 6.0% |
| Alkylbenzene sulfonate Na | 12.0% | 12.0% |
| Cellulose powder | 3.0% | 3.0% |
| Na citrate (dihydrate) | 3.5% | 3.5% |
| $Na_2SO_4$ | 24.9% | 14.9% |
| $Na_2CO_3$ | 2.0% | 2.0% |
| Perfume oil | 6.0% | 6.0% |
| $C_{16}$ Fatty alcohol | 4.0% | 4.0% |
| Lipase* | 10.0% | 20.0% |
| Total weight 50 g: | Shell 25 g | Core 25 g |

*From Gist-Brocades BSD BV, Netherlands

The powder-form raw materials of the shell and core were mixed in two separate mixers. Lipase was then introduced. The mixtures were stored in two silos. The two mixtures were introduced into extruders 1 (shell) and 2 (core) via two weighing belts, perfume oil being introduced into extruders 1 and 2 via metering pumps for plastication. The strands were combined in a ratio by weight of 1:1 in the multicomponent nozzle and cut to the required length. The shape corresponded to FIG. 1 with dimensions of approximately 16×28×80 mm.

EXAMPLE 20:

Cistern block with enzymes

| Raw material | Shell | Core |
|---|---|---|
| Sodium lauryl sulfate | 11.4% | 11.4% |
| Cocofatty acid monoethanolamide | 8.5% | 8.5% |
| Na citrate (dihydrate) | 9.0% | 18.5% |
| $Na_2SO_4$ | 48.3% | 29.8% |
| $Na_2CO_3$ | 0.8% | 0.8% |
| Acid Blue 9 | 4.0% | 4.0% |
| Sodium stearate | 2.0% | 3.0% |
| Perfume oil spruce note | 6.0% | 6.0% |
| Protease* | 5.0% | 8.0% |
| Lipase* | 5.0% | 10.0% |
| Total weight 100 g: | Shell 60 g | Core 40 g |

*From Gist-Brocades BSD BV, Netherlands

Figure 6:
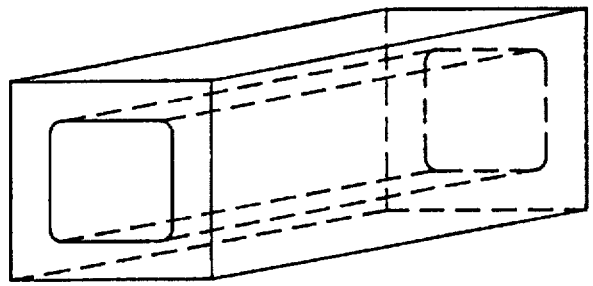

The raw materials, except for the enzymes, were mixed and kneaded in separate Z-kneaders with addition of the perfume to batch sizes of 300 and 200 kg. The enzymes were then added, followed by brief mixing. The two components were introduced into a molding press through two extruders, extruded through a twin die ring and cut into cubes with an edge length of about 34 mm (FIG. 6).

What is claimed is:

1. A block-form cleaner for flush toilets comprising at least two masses of different composition, one of the masses being at least partly surrounded by the other mass or masses, and wherein the surrounded mass and at least one of the surrounding masses contain at least one identical active substance selected from the group consisting of perfume, complexing agent, acid, enzyme, disinfectant, bleaching agent, and mixtures thereof, and the concentration of at least one of these identical active substances in the surrounded mass is at least 1.3 times the concentration of the same active substance In the at least one surrounding mass, wherein each mass contains from 7 to about 85% by weight of surfactant, wherein none of the masses contains a soap in a quantity of greater than 25% by weight, based on the weight of the mass and wherein the masses are constructed so that only or preponderantly the surface of the mass containing the identical active substance in the lower concentrations is initially available for the release of said identical active substance to the surrounding environment.

2. The block-form cleaner of claim 1 wherein said concentration in the surrounded mass is from about 2 to about 10 times the concentration in the surrounding mass.

3. The block-form cleaner of claim 1 wherein at least 50% of the surface of the surrounded mass is covered by the surrounding mass or masses.

4. The block-form cleaner of claim 1 wherein at least 70% of the surface of the surrounded mass is covered by the surrounding mass or masses.

5. The block-form cleaner of claim 1 wherein at least 80% of the surface of the surrounded mass is covered by the surrounding mass or masses.

6. The block-form cleaner of claim 1 wherein said identical active substance is a perfume.

7. The block-form cleaner of claim 1 wherein the surrounded mass is surrounded by only one surrounding mass.

8. The block-form cleaner of claim I wherein the surrounded mass is positioned relative to the surrounding mass or masses so that during use the surface of the surrounded mass gradually becomes larger.

9. The block-form cleaner of claim 2, wherein at least 50% of the surface of the surrounded mass is covered by the surrounding mass or masses.

10. The block-form cleaner of claim 9 wherein at least 70% of the surface of the surrounded mass is covered by the surrounding mass or masses.

11. The block-form cleaner of claim 10 wherein the surrounded mass is surrounded by only one surrounding mass.

12. The block-form cleaner of claim 11 wherein the surrounded mass is positioned relative to the surrounding mass so that during use the surface of the surrounded mass gradually becomes larger.

13. The block-form cleaner of claim 1 wherein at least one mass contains from about 2 to about 25% by weight of an erosion regulator selected from the group consisting of solid long chain fatty acids, salts of solid long chain fatty acids, fatty acid ethanolamides, $C_{12-18}$ fatty alcohols, and solid polyethylene glycols.

14. A method for the manufacture of the block-form cleaner of claim 1 comprising the steps of:

I) separately producing mixtures of components comprising the respective masses; and II) pressing together the separate mixtures to form said block-form cleaner.

15. A method for the manufacture of the block-form cleaner of claim comprising the steps of:

I) forming a mixture of components of at least one mass and molding the at least one mass into a molded shape; and II) adding another mass in liquid form thereto; and III) solidifying the added liquid mass to form the block-form cleaner.

16. A method for the manufacture of the block-form cleaner of claim 1 comprising the steps of:

I) forming separate mixtures of the components of the respective masses;

II) extruding the separate mixtures into strands;

III) combining and shaping the strands; and

IV) cutting strands to directly form the block-form cleaner.

17. The method of claim 16 wherein in steps II and III the mixture containing the active substance in the higher concentration is extruded as a core strand inside a surrounding shell-like strand of the mixture containing the active substance in the lower concentration.

* * * * *